(12) United States Patent
Garvey et al.

(10) Patent No.: US 11,839,388 B2
(45) Date of Patent: *Dec. 12, 2023

(54) SURGICAL ALIGNMENT GUIDE ASSEMBLY FOR TOTAL ANKLE REPLACEMENT AND METHOD OF USING THE SAME

(71) Applicant: restor3d, Inc., Durham, NC (US)

(72) Inventors: Brian Garvey, Bryn Mawr, PA (US); Deepak Padmanabhan, Philadelphia, PA (US); Gerard Cush, Danville, PA (US); Dhwanit Vispute, Philadelphia, PA (US)

(73) Assignee: RESTOR3D, INC., Durham, NC (US)

( * ) Notice: Subject to any disclaimer, the term of this patent is extended or adjusted under 35 U.S.C. 154(b) by 2 days.

This patent is subject to a terminal disclaimer.

(21) Appl. No.: 17/711,418

(22) Filed: Apr. 1, 2022

(65) Prior Publication Data

US 2023/0000504 A1   Jan. 5, 2023

Related U.S. Application Data

(63) Continuation of application No. 17/363,471, filed on Jun. 30, 2021, now Pat. No. 11,324,525.

(51) Int. Cl.
  *A61B 17/17*  (2006.01)
(52) U.S. Cl.
  CPC ...... *A61B 17/1775* (2016.11); *A61B 17/1796* (2013.01)

(58) Field of Classification Search
  CPC ............ A61B 17/1775; A61B 17/1796; A61B 17/1721; A61B 17/1725; A61B 17/1728; A61B 17/1757; A61B 17/1764; A61B 17/1782
  See application file for complete search history.

(56) References Cited

U.S. PATENT DOCUMENTS

| | | | |
|---|---|---|---|
| 7,468,075 B2 | 12/2008 | Lang et al. |
| 7,534,263 B2 | 5/2009 | Burdulis, Jr. et al. |
| 7,618,451 B2 | 11/2009 | Berez et al. |
| 7,634,119 B2 | 12/2009 | Tsougarakis et al. |
| 7,717,956 B2 | 5/2010 | Lang |
| 7,796,791 B2 | 9/2010 | Tsongarakis et al. |
| 7,799,077 B2 | 9/2010 | Lang et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,077,950 B2 | 12/2011 | Tsougarakis et al. |
| 8,083,745 B2 | 12/2011 | Lang et al. |

(Continued)

FOREIGN PATENT DOCUMENTS

| | | | | |
|---|---|---|---|---|
| CN | 109567913 A | 4/2019 | | |
| WO | WO-2014020562 A1 * | 2/2014 | ............. | A61B 17/15 |
| WO | 2020123295 A1 | 6/2020 | | |

*Primary Examiner* — Amy R Sipp
(74) *Attorney, Agent, or Firm* — Husch Blackwell LLP; Bryan D. Stewart; Andrew C. Landsman

(57) ABSTRACT

A surgical guide assembly is disclosed herein that includes instruments configured to aid in the alignment of surgical instruments. In one aspect, a first and second instrument are provided that are configured to be connected to each other via interfaces and each define bone contact interface. The bone contact interfaces are configured to engage with the tibia and talus, in one embodiment.

11 Claims, 12 Drawing Sheets

(56) References Cited

U.S. PATENT DOCUMENTS

| | | |
|---|---|---|
| 8,094,900 B2 | 1/2012 | Steines et al. |
| 8,105,330 B2 | 1/2012 | Fitz et al. |
| 8,234,097 B2 | 1/2012 | Steines et al. |
| 8,122,582 B2 | 2/2012 | Burdulis, Jr. et al. |
| 8,337,501 B2 | 12/2012 | Fitz et al. |
| 8,337,507 B2 | 12/2012 | Lang et al. |
| 8,343,218 B2 | 1/2013 | Lang et al. |
| 8,366,771 B2 | 2/2013 | Burdulis, Jr. et al. |
| 8,377,129 B2 | 2/2013 | Fitz et al. |
| 8,439,926 B2 | 5/2013 | Bojarski et al. |
| 8,460,304 B2 | 6/2013 | Fitz et al. |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski et al. |
| 8,545,569 B2 | 10/2013 | Fitz et al. |
| 8,551,099 B2 | 10/2013 | Lang et al. |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,585,708 B2 | 11/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 8,690,945 B2 | 4/2014 | Fitz et al. |
| 8,709,089 B2 | 4/2014 | Lang et al. |
| 8,735,773 B2 | 5/2014 | Lang |
| 8,768,028 B2 | 7/2014 | Lang et al. |
| 8,771,365 B2 | 7/2014 | Bojarski et al. |
| 8,882,847 B2 | 11/2014 | Burdulis, Jr. et al. |
| 8,906,107 B2 | 12/2014 | Bojarski et al. |
| 8,926,706 B2 | 1/2015 | Bojarski et al. |
| 8,932,363 B2 | 1/2015 | Tsougarakis et al. |
| 8,945,230 B2 | 2/2015 | Lang et al. |
| 8,951,259 B2 | 2/2015 | Fitz et al. |
| 8,951,260 B2 | 2/2015 | Lang et al. |
| 8,965,088 B2 | 2/2015 | Tsougarakis et al. |
| 8,974,539 B2 | 3/2015 | Bojarski et al. |
| 8,998,915 B2 | 4/2015 | Fitz et al. |
| 9,020,788 B2 | 4/2015 | Lang et al. |
| 9,023,050 B2 | 5/2015 | Lang et al. |
| 9,055,953 B2 | 6/2015 | Lang et al. |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| 9,095,353 B2 | 8/2015 | Burdulis, Jr. et al. |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,125,673 B2 | 9/2015 | Fitz et al. |
| 9,180,015 B2 | 11/2015 | Fitz et al. |
| 9,186,161 B2 | 11/2015 | Lang et al. |
| 9,186,254 B2 | 11/2015 | Fitz et al. |
| 9,216,025 B2 | 12/2015 | Fitz et al. |
| 9,220,516 B2 | 12/2015 | Lang et al. |
| 9,220,517 B2 | 12/2015 | Lang et al. |
| 9,241,724 B2 | 1/2016 | Lang et al. |
| 9,241,725 B2 | 1/2016 | Lang et al. |
| 9,295,482 B2 | 3/2016 | Fitz et al. |
| 9,308,005 B2 | 4/2016 | Fitz et al. |
| 9,308,053 B2 | 4/2016 | Bojarski et al. |
| 9,308,091 B2 | 4/2016 | Lang |
| 9,314,256 B2 | 4/2016 | Fitz et al. |
| 9,320,620 B2 | 4/2016 | Bojarski et al. |
| 9,295,481 B2 | 5/2016 | Fitz et al. |
| 9,326,780 B2 | 5/2016 | Wong et al. |
| 9,333,058 B1 | 5/2016 | Krastev |
| 9,358,018 B2 | 6/2016 | Fitz et al. |
| 9,375,222 B2 | 6/2016 | Fitz et al. |
| 9,387,079 B2 | 6/2016 | Bojarski et al. |
| 9,381,025 B2 | 7/2016 | Fitz et al. |
| 9,402,726 B2 | 8/2016 | Linderman et al. |
| 9,408,615 B2 | 8/2016 | Fitz et al. |
| 9,408,686 B1 | 8/2016 | Miller et al. |
| 9,439,767 B2 | 9/2016 | Bojarski et al. |
| 9,486,226 B2 | 11/2016 | Chao |
| 9,495,483 B2 | 11/2016 | Steines et al. |
| 9,517,134 B2 | 12/2016 | Lang |
| 9,579,110 B2 | 2/2017 | Bojarski et al. |
| 9,603,711 B2 | 3/2017 | Bojarski et al. |
| 9,636,229 B2 | 5/2017 | Lang et al. |
| 9,675,471 B2 | 6/2017 | Bojarski et al. |
| 9,681,956 B2 | 6/2017 | Al Hares et al. |
| 9,687,945 B2 | 6/2017 | Steines et al. |
| 9,700,420 B2 | 7/2017 | Fitz et al. |
| 9,700,971 B2 | 7/2017 | Lang |
| 9,737,367 B2 | 8/2017 | Steines et al. |
| 9,775,680 B2 | 10/2017 | Bojarski et al. |
| 9,849,019 B2 | 12/2017 | Miller et al. |
| 9,872,773 B2 | 1/2018 | Lang et al. |
| 9,877,790 B2 | 1/2018 | Bojarski et al. |
| 9,913,723 B2 | 3/2018 | Fitz et al. |
| 9,943,370 B2 | 4/2018 | Asseln et al. |
| 9,956,047 B2 | 5/2018 | Bojarski et al. |
| 9,956,048 B2 | 5/2018 | Bojarski et al. |
| 10,085,839 B2 | 10/2018 | Wong et al. |
| 11,324,525 B1* | 5/2022 | Garvey .............. A61B 17/1796 |
| 2013/0296874 A1* | 11/2013 | Chao .................... A61B 17/157 606/88 |
| 2018/0289380 A1* | 10/2018 | Mauldin ................ A61B 17/15 |
| 2020/0085452 A1* | 3/2020 | Siegler ............... A61B 17/1703 |
| 2020/0367910 A1 | 11/2020 | Hafez et al. |
| 2021/0077276 A1 | 3/2021 | Garvey et al. |

\* cited by examiner

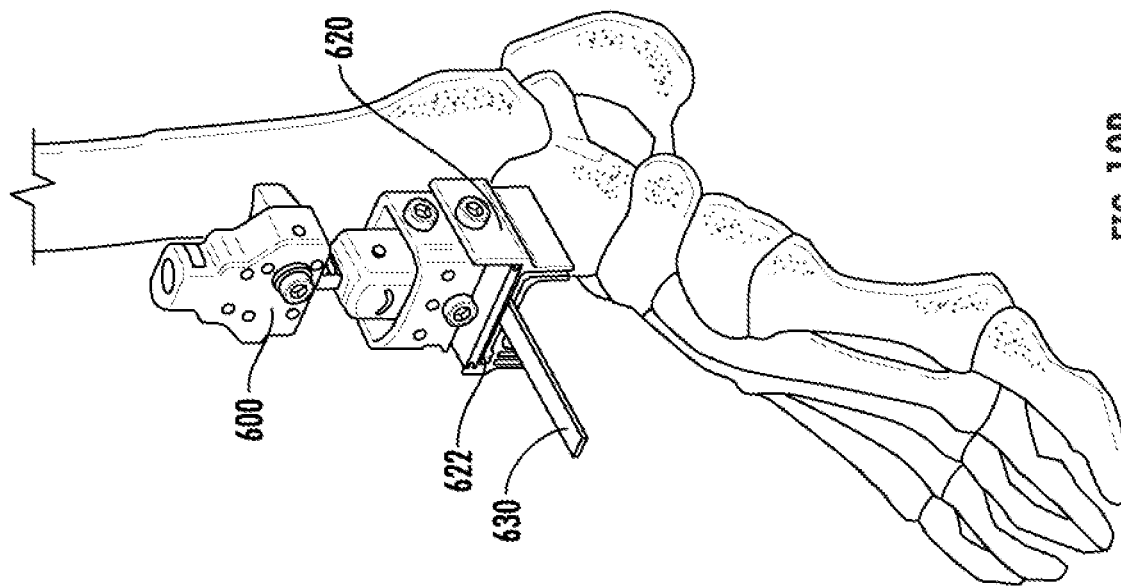
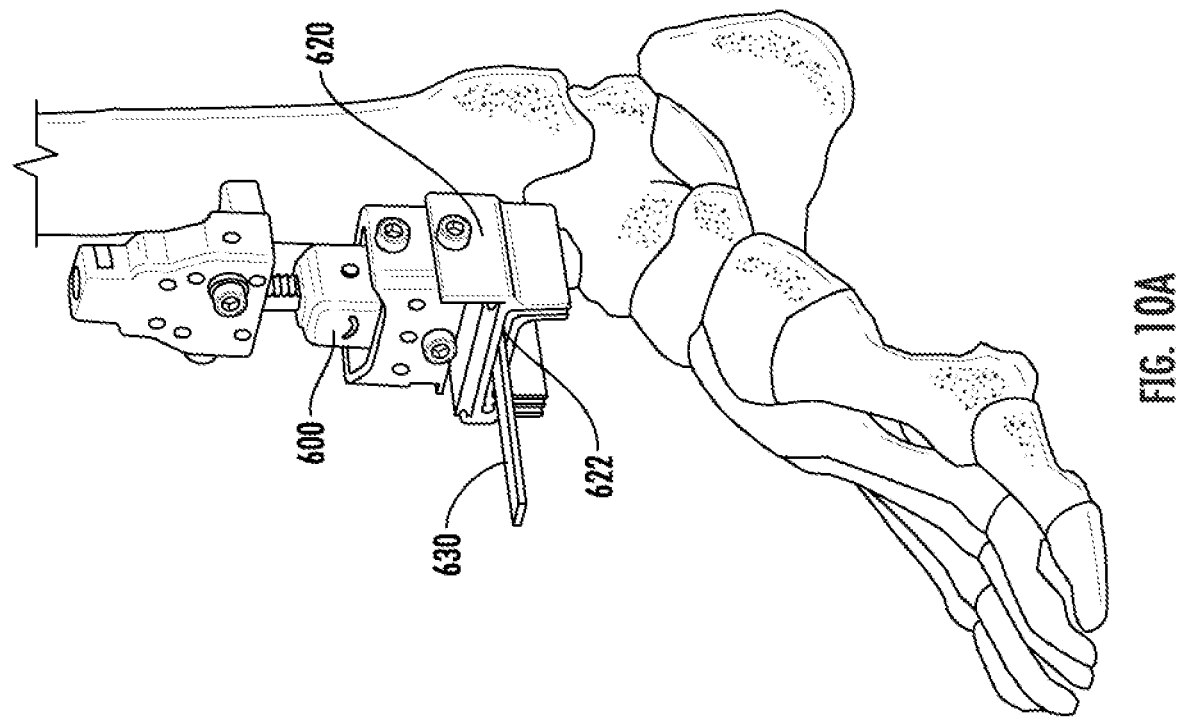

SURGICAL ALIGNMENT GUIDE ASSEMBLY FOR TOTAL ANKLE REPLACEMENT AND METHOD OF USING THE SAME

INCORPORATION BY REFERENCE

This application is a continuation application of U.S. patent application Ser. No. 17/363,471, filed on Jun. 30, 2021, the entire contents of which is incorporated herein by reference as if fully set forth.

FIELD OF INVENTION

The present disclosure relates to tools and methods for performing ankle replacement surgery.

BACKGROUND

Ankle replacement surgery is a procedure for treating patients with end stage ankle arthritis, rheumatoid arthritis and other painfully arthritic conditions of the ankle or other maladies. Total ankle replacement (TAR), as it is commonly referred to, is typically not as clinically successful as other total joint replacements (i.e. knee, hip, shoulder). The failure rates of TAR procedures are sometimes two or three times greater than total knee or total hip replacement.

One of the more difficult aspects of a TAR procedure is manually aligning the patient's ankle joint so that the surgeon may make the appropriate bone resection cuts. The location and accuracy of the bone resection cuts determine the location of the total ankle implant and ultimately determine how well the implant will function and to what extent the patient's quality of life has improved. Accordingly, making accurate incisions is critical to a successful surgery and recovery.

The ankle joint must be appropriately aligned with long axis of the tibial bone in order to place the implant where it will most effectively provide the requisite range of motion and counteract the forces experienced in daily activities, such as walking, jogging, standing, etc. There are six degrees of freedom that must be aligned by the surgeon during the surgery. The alignment of the ankle joint is achieved with instruments used to prepare the tibial and talar bones in preparation of implant placement.

It would be desirable to provide instruments and tools that ensure surgeons and other medical personnel can perform reliable and accurate alignment of a patient's ankle joint prior to and during surgery.

SUMMARY

Surgical guide assemblies, methods, and modular systems are disclosed herein that generally aid with alignment of tools and instruments during surgical procedures.

In one aspect, a surgical guide is disclosed. The surgical guide includes at least one first surgical instrument having at least one first bone contact interface configured to mate with at least a portion of a patient's bony anatomy, and at least one first connection interface configured to mate with at least one connection interface formed on different surgical instruments. At least one second surgical instrument is also provided. The second surgical instrument includes at least one second bone contact interface configured to mate with at least a portion of the patient's bony anatomy, and at least one second connection interface configured to mate with the at least one first connection interface such that the at least one first surgical instrument and the at least one second surgical instrument are linked to form an assembly.

When both the at least one first surgical instrument and the at least one second surgical instrument are contacting a patient's bony anatomy, the assembly is oriented in a predetermined manner relative to the patient's bony anatomy.

A third surgical instrument is also included that has at least one third connection interface configured to mate with the at least one first connection interface, at least one guide opening or aperture for guiding at least one fourth surgical instrument, and at least one adjustable mechanism configured to reposition the at least one guide opening or aperture relative to the patient's bony anatomy.

A method of aligning at least one surgical instrument including at least one guide opening is also provided. The method can include providing at least one first surgical instrument and at least one second surgical instrument. The method includes arranging at least one of the at least one first surgical instrument and the at least one second surgical instrument on a patient's bone. The method also includes linking the at least one first surgical instrument and the at least one second surgical instrument with each other to form an assembly. Next, the method includes removing the at least one second surgical instrument from the at least one bone, leaving the at least one first surgical instrument in a desired alignment position relative to the patient. The method also includes aligning at least one third surgical instrument with the at least one first surgical instrument and with the at least one bone of the patient, and linking the at least one third surgical instrument with the at least one first surgical instrument. The at least one third surgical instrument includes at least one guide opening, and the method includes guiding at least one fourth surgical instrument through the at least one guide opening.

In another embodiment, a surgical guide is provided. The surgical guide includes at least one first surgical instrument comprising at least one first bone contact interface configured to mate with a portion of bone and at least one first connection interface. The surgical guide also includes at least one second surgical instrument comprising at least one second bone contact interface configured to mate with a portion a bone, and a second connection interface configured to mate with the at least one first surgical instrument to form an assembly. The assembly of the at least one first surgical instrument and the at least one second surgical instrument is oriented in a predetermined manner relative to the patient's bony anatomy when both the at least one first surgical instrument and the at least one second surgical instrument are contacting a patient's bony anatomy.

A method of aligning surgical instruments relative to a patient is also provided. The method includes providing a first instrument including a first bone contact interface and a second bone contact interface, the first bone contact interface and the second bone contact interface each being configured to contact a different bone in a patient. The first surgical instrument further includes a first connection interface configured to mechanically link the first instrument with at least two other instruments. A second instrument is also provided that includes a second connection interface configured to mate with the first connection interface and a third bone contact interface configured to contact the same bone as the first bone contact interface. At least one third instrument is also provided that defines an aperture or guide opening configured to receive a cutting tool. The at least one third instrument also includes a third connection interface that is also configured to mate with the first connection interface. The method includes connecting the first instrument and the second instrument, and arranging the first instrument and the second instrument in contact with a patient's bony anatomy. The method includes removing the second instrument from the first instrument such that the first instrument remains engaged with the patient's bony anatomy. The method then includes attaching the third instrument to the first instrument, and removing the first instrument from the third instrument such that the third instrument remains engaged with the patient's bony anatomy.

Other embodiments are disclosed herein.

BRIEF DESCRIPTION OF THE DRAWINGS

The foregoing Summary and the following Detailed Description will be better understood when read in conjunction with the appended drawings, which illustrate a preferred embodiment of the invention. In the drawings:

FIGS. 10A and 10B are perspective views of the third and fifth instruments deployed to the patient's anatomy as used in connection with a fourth instrument.

DETAILED DESCRIPTION OF THE PREFERRED EMBODIMENTS

Figure 1A:
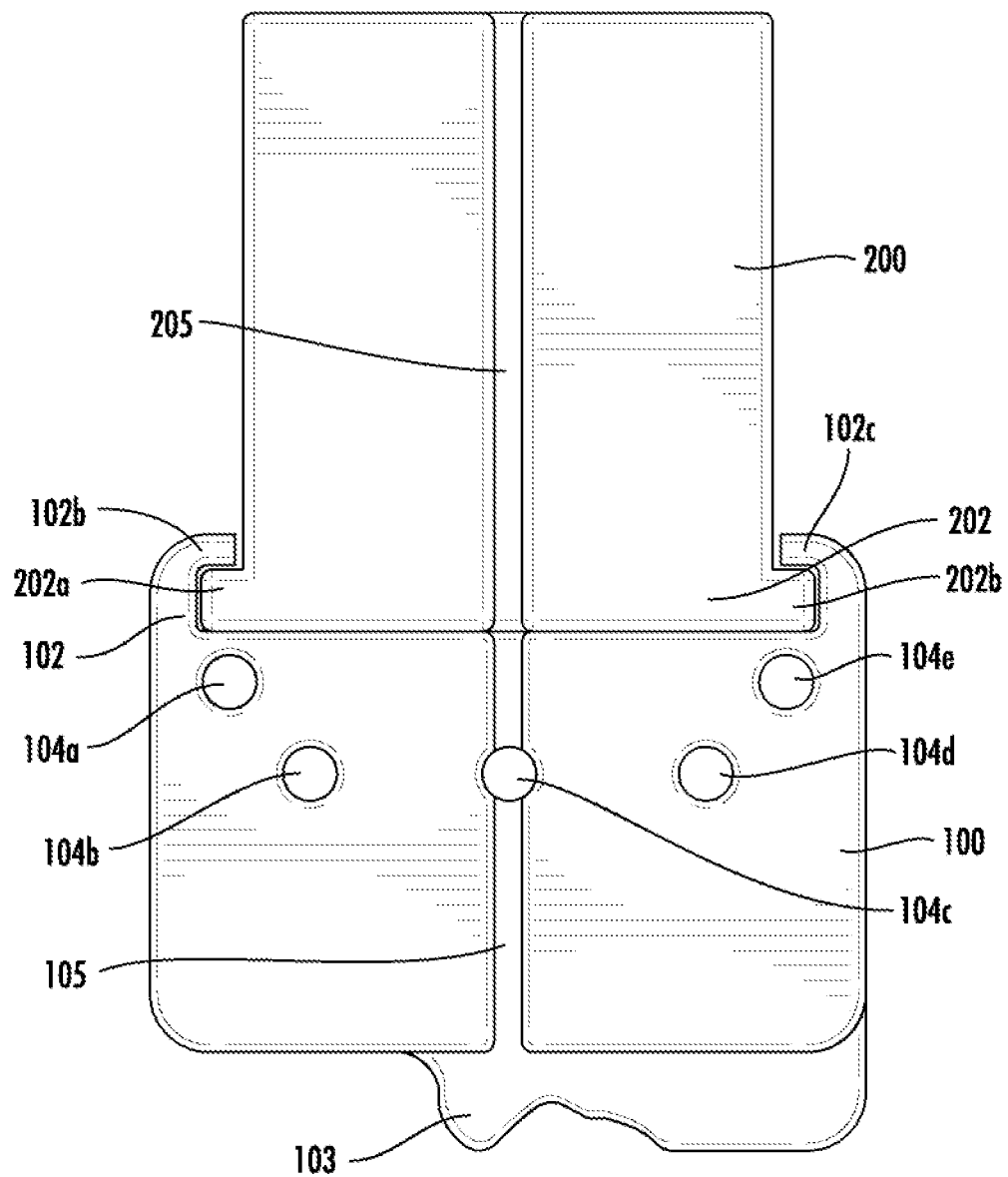
FIG. 1A is an anterior view of a first and second instrument mated with each other.
Figure 1B:
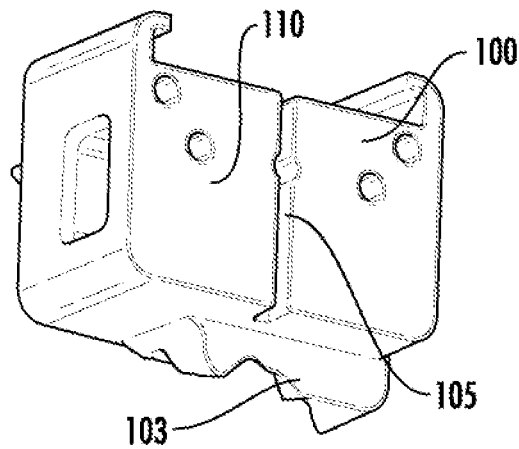
FIG. 1B is a first perspective view of the first instrument.

In general, total ankle replacement surgery requires that a patient is placed supine on an operating table support. A protrusion or bump can be placed under the patient's calf to maintain proper rotation of the patient's leg. The patient's patella is arranged to face directly anterior. General or regional anesthesia may be used. If using regional anesthesia, the sciatic or popliteal catheter must be positioned in a way that does not interfere with the surgery. A thigh tourniquet is generally used proximal to the popliteal catheter. Intravenous antibiotics and sequential compression are used on the contralateral leg. The leg is prepared and draped using proper sterile technique, leaving the knee to foot exposed. Exsanguination is performed prior to tourniquet activation.

A skin incision is made just lateral to the tibial crest from approximately 6 cm proximal of the tibial plafond, and extending distal up to the talonavicular joint. The superficial peroneal nerve is identified and mobilized laterally. The extensor retinaculum and extensor hallucis longus (EHL) tendon sheath are exposed, but the anterior tibial tendon sheath cannot be exposed. The deep peroneal nerve and artery are then identified and mobilized laterally. It is important to protect these structures throughout the procedure. Finally, the ankle joint capsule is incised longitudinally and exposed from the medial malleolus to the syndesmosis. Osteophytes on the neck of the talus and anterior tibia must be removed. It is important to avoid weakening the underlying bone by removing too much substrate. If a varus deformity requires correction, a deltoid release is performed. It is important to release the talar deltoid attachment from anterior to posterior as a single structure. As explained above, these surgeries and procedures are complicated and require that surgeons can correctly, accurately, and precisely have access to specific portions of the patient's anatomy. Accordingly, the subject matter disclosed herein provides an improved tool, process, and method of aligning surgical instruments and tools relative to a patent.

Aspects and embodiments of a surgical guide are disclosed herein that aid surgeons in operating on patients during surgeries, such as total ankle replacement surgeries.

A first surgical instrument 100 and a second surgical instrument 200 are generally illustrated in FIGS. 1A-1I. These two instruments 100, 200 are generally configured to work in conjunction with each other to aid in the alignment of tools and instruments relative to a patient's anatomy.

In one embodiment, the first surgical instrument 100 has a first bone contact interface 101 that is configured to engage with a least a portion of a patient's bones, such as a first bone 300 of a patient. The first bone 300 can be the tibia, or any other bone.

As used herein, the terms surgical instrument, instrument or tool are used interchangeably. Additionally, in one aspect, the term instrument refers to a modular tool that primarily is configured to both engage with other tools or instruments and also is configured to interact with a patient, either via bone contacting surfaces, apertures for receiving guide wires or K-wires, slots configured to receive cutting tools, or other features.

Figure 1C:
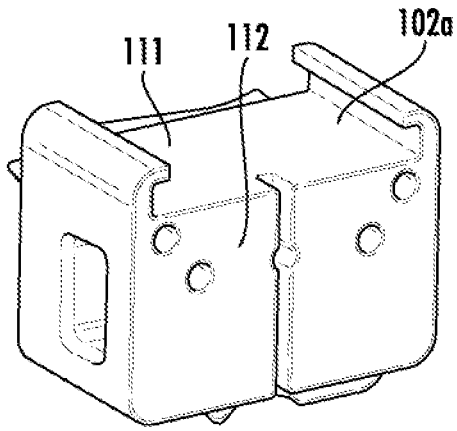
FIG. 1C is a second perspective view of the first instrument.
Figure 1D:
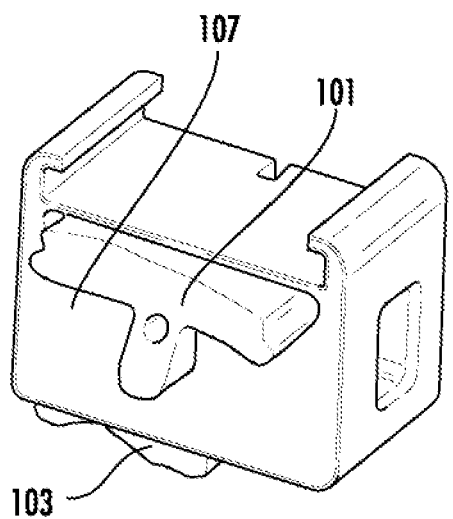
FIG. 1D is a third perspective view of the first instrument.
Figure 1E:
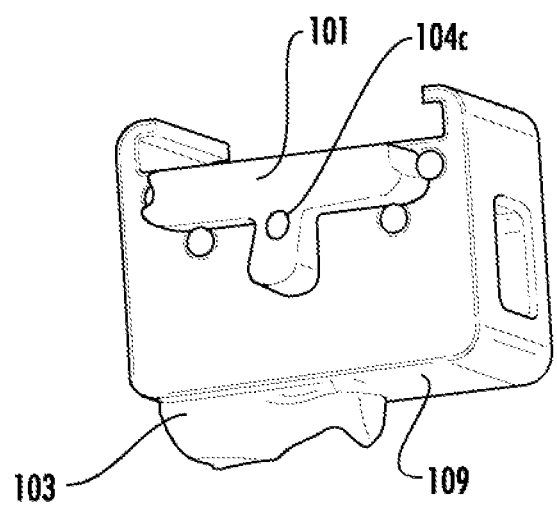
FIG. 1E is a fourth perspective view of the first instrument.
Figure 1F:
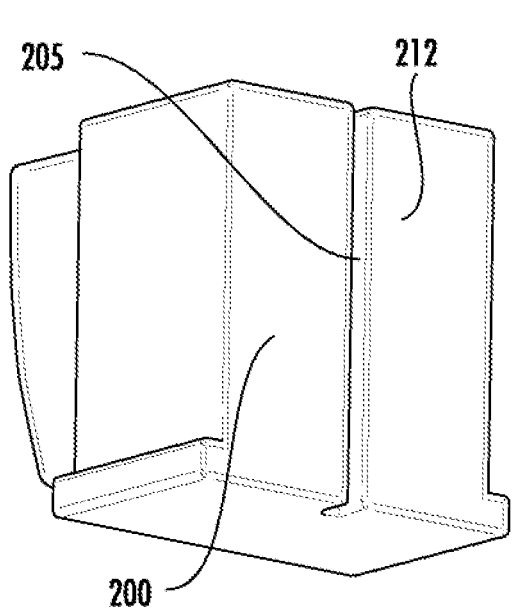
FIG. 1F is a first perspective of the second instrument.
Figure 1G:
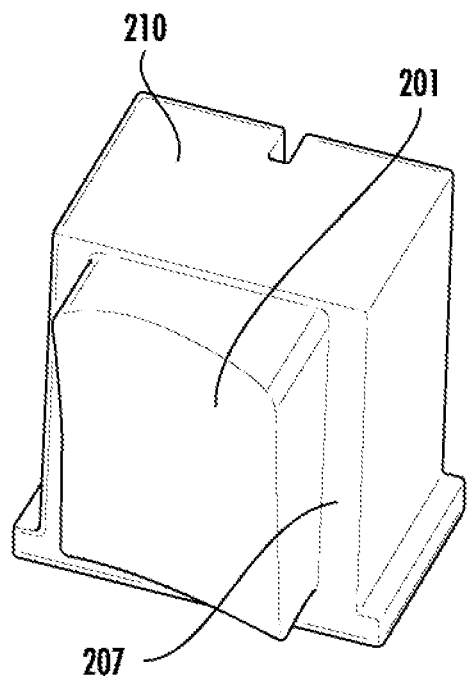
FIG. 1G is a second perspective view of the second instrument.
Figure 1H:
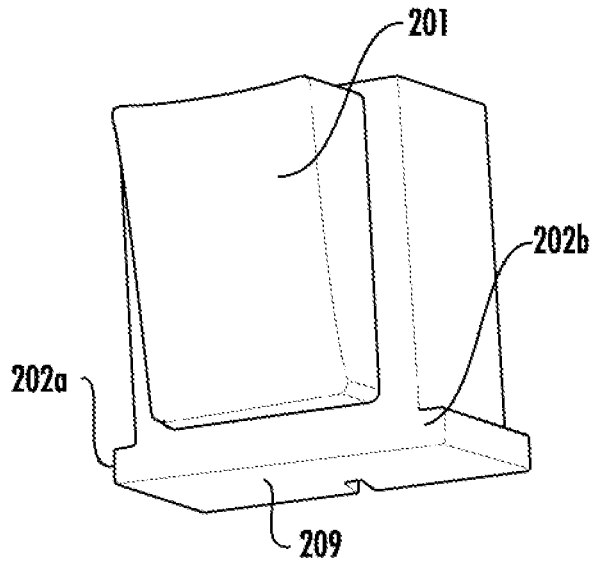
FIG. 1H is a third perspective view of the second instrument.
Figure 1I:
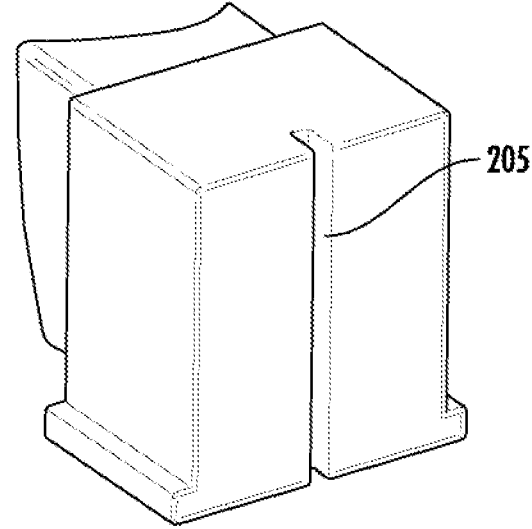
FIG. 1I is a fourth perspective view of the second instrument.
Figure 2:
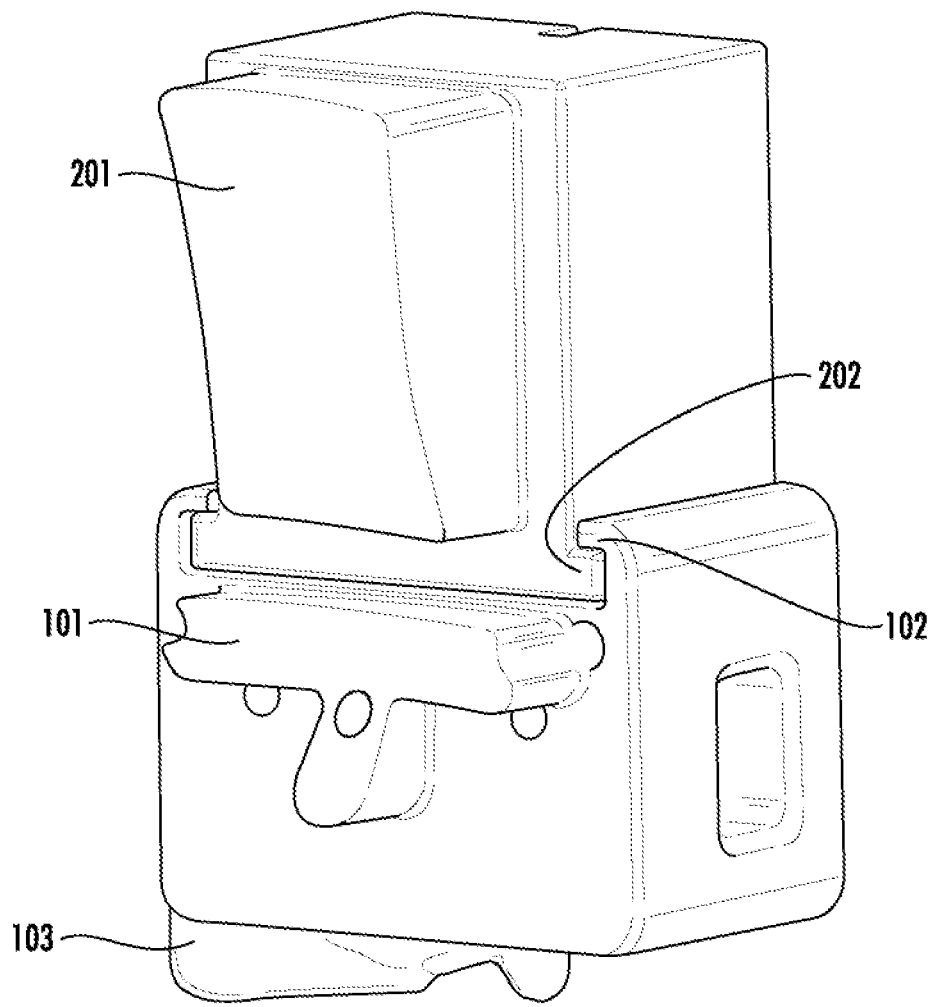
FIG. 2 is a perspective view of an embodiment of the first and second instruments mated with each other.
Figure 3:
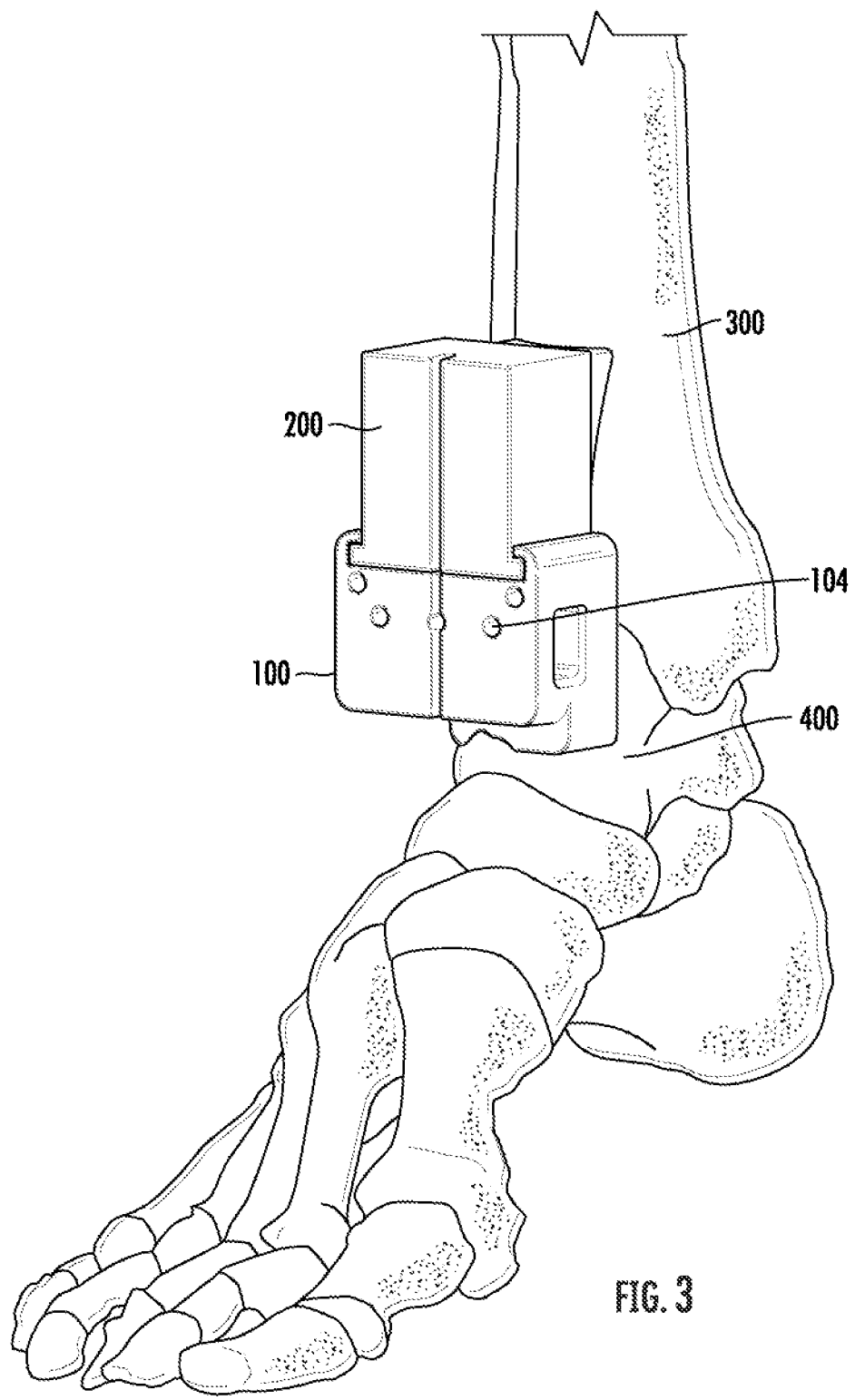
FIG. 3 is another perspective isometric view of the first and second instruments positioned relative to a patient's anatomy.

In one aspect, the first bone contact interface 101 is configured to contact, interface, or mate with a patient's tibia. One skilled in the art would understand that the first bone contact interface 101 can be configured to contact, interface, or mate with other bones or patient anatomy. The first bone contact interface 101 generally includes a curved surface, as shown in FIGS. 1D, 1E, and 2. The specific profile and geometry of the first bone contact interface 101 can be precisely selected to match a patient's anatomy using imaging techniques. In other words, the first bone contact interface 101 can be customized or tailored to match a patient's geometry. In one aspect, this process is based on a negative mold of a patient's anatomy, which can be based on electronic imaging data or other techniques.

The first surgical instrument 100 also includes a connection interface 102, which is also referred to as a first connection interface. In one aspect, the connection interface 102 is a surface designed to allow the first surgical instrument 100 to mate or connect with additional surgical instruments. In one aspect, the connection interface 102 can include a slot 102a including a pair of arms 102b, 102c. In one aspect, the slot 102a is configured to receive a protrusion. One of ordinary skill in the art would understand that alternatively, the connection interface 102 can be a protrusion and a slot can be formed on another instrument to connect with the protrusion. As shown in FIG. 1C, each of the arms 102b, 102c extend for an entire edge of a base body 110 of the first instrument 100. Other types of connection interfaces can be used.

The first surgical instrument 100 can also comprise a second bone contact interface 103 configured to mate with a second bone of a patient 400, such as the talus. The specific profile and geometry of the second bone contact interface 103 can be precisely selected to match a patient's anatomy using imaging techniques. In other words, the second bone contact interface 103 can be customized or tailored to match a patient's geometry. In one aspect, this process is based on a negative mold of a patient's anatomy, which can be based on electronic imaging data or other techniques.

Figure 5:
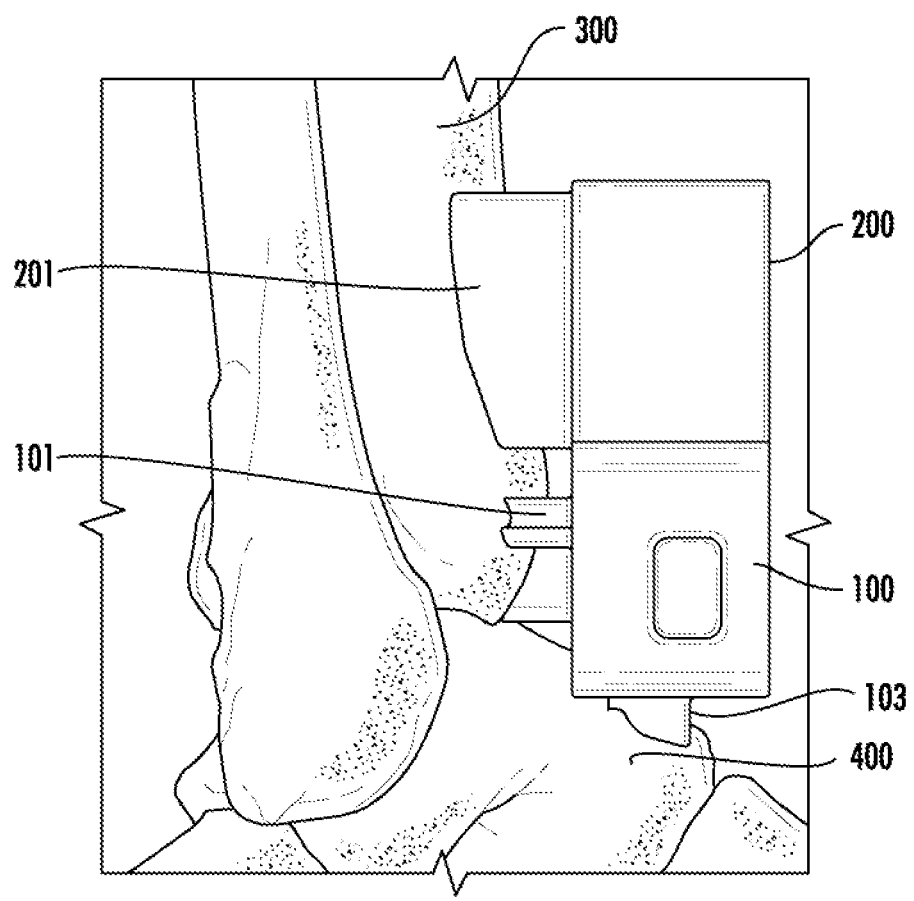
FIG. 5 is a lateral view of the first and second instruments in position relative to a patient's anatomy.

A joint or interface is defined between the first bone 300 and the second bone 400. As shown in FIG. 5, in one aspect, the first surgical instrument 100 is configured to engage a lower region of the first bone 300 (i.e. the tibia) via the first bone contact interface 101 and also contact an upper portion of the second bone 400 (i.e. the talus) via the second bone contact interface 103. In this respect, the first surgical instrument 100 can be configured to contact two bone surfaces on two different bones 300, 400.

The second surgical instrument 200 is configured to engage or contact an upper region of the first bone 300 (i.e. the tibia) via its bone contact interface 201. As shown in FIG. 5, the first bone contact interface 101 of the first surgical instrument 100 and the bone contact interface 201 of the second surgical instrument 200 can be configured to contact a same side or face of the first bone 300. In one aspect, the first surgical instrument 100 is configured to contact two bones that have opposing joint surfaces between them. In one aspect, adjustments made using the instruments disclosed herein are primarily directed to adjustments relative to the first bone 300.

In one aspect, at least one aperture 104, 104a, 104b, 104c, 104d, 104e may be provided on the first instrument 100. The apertures 104, 104a, 104b, 104c, 104d, 104e can each be configured to receive or accept a stabilizing component, such as k-wire, a drill, a pin, a screw, or other component used to stabilize the first instrument 100 to the first bone 300 of the patient or the second bone 400 of the patient. As shown in FIG. 1E, at least one of the apertures 104c is defined within the first bone contact interface 101. One skilled in the art would understand that other apertures could also be defined on the first bone contact interface 101.

In one aspect, an alignment feature 105 may be provided on the first surgical instrument 100. The alignment feature 105, which is also referred to as a first alignment feature 105, can be defined on an opposite lateral side 112 of the base body 110 as the first bone contact interface 101. In one aspect, the alignment feature 105 is configured to aid in the alignment of at least one other instrument. For example, the alignment feature 105 can be used for the alignment with or between at least one of: the second surgical instrument 200, the first surgical instrument 100 relative to the first bone 300, or the first surgical instrument 100 relative to one or more of the other bones (such as bones 500, 501, 502) of the foot or bones of the leg or other anatomic location, such as the knee or femur. The alignment feature 105 can be formed as a slot that extends for an entire face of the base body 110 and between two edges of the base body 110. In one aspect, the alignment feature 105 overlaps with at least one aperture 104c.

In one aspect, the first surgical instrument 100 generally has a rectangular or square shaped base body 110. The exact shape of the first surgical instrument 100 can vary, as would be appreciated by one of ordinary skill in the art based on the present disclosure. The first bone contact interface 101 protrudes outward from a lateral side 107 of the base body 110 in one aspect. The second bone contact interface 103 similarly protrudes from the base body 110. The second bone contact interface 103 protrudes from a bottom surface 109 of the base body 110, in one aspect. The second bone contact interface 103 can protrude from other sides or surfaces of the base body 110. The connection interface 102 can be defined on a top surface 111 of the base body 110, which is opposite from the bottom surface 109 partially defining the second bone contact interface 103.

The second surgical instrument 200 generally has a square or rectangular base body 210, in one embodiment. The second surgical instrument 200 includes a corresponding mating surface or connection interface 202 that is configured to mate or connect with the connection interface 102 of the first surgical instrument 100. The connection interface 202 is also referred to as a second connection interface herein. As shown in FIG. 1A, the second connection interface 202 can include a pair of protrusions or protruding flanges 202a, 202b dimensioned to be slid under the arms 102a, 102b. One of ordinary skill in the art would understand that the first surgical instrument 100 could include protruding flanges and the second surgical instrument 200 could include a slot configured to receive the protruding flanges. Additionally, other types of mating interfaces can be used. In one aspect, the second connection interface 202 is formed on a bottom surface 209 of the base body 210.

Additional details of the second surgical instrument 200 are shown in FIGS. 1F-1I. The second surgical instrument 200 can include a bone contact interface 201 that is configured to engage a patient's bone or anatomy. The bone contact interface 201 is also referred to as a third bone contact interface 201 herein. The bone contact interface 201 can be defined on a lateral side or surface 207 of the base body 210. In one aspect, the bone contact interface 201 is configured to contact the same bone that the bone contact interface 101 contacts. The bone contact interface 201 can have a generic profile that is not specifically shaped to match a specific patient. In another aspect, the bone contact interface 201 can be specifically custom made for a particular patient's geometry, such as via 3-D modeling or digital imaging.

In one aspect, the first instrument 100 includes exactly two bone contact interfaces 101, 103 and the second instrument 200 includes exactly one bone contact interface 201. One of ordinary skill in the art would understand that these bone contact interfaces can vary.

The second surgical instrument 200 can include an alignment feature 205 that is configured to be used in conjunction with the first alignment feature 105. The alignment feature 205 is also referred to as a second alignment feature 205 herein. In one aspect, the alignment feature 205 is defined on a lateral side 212 of the base body 210.

Figure 4:
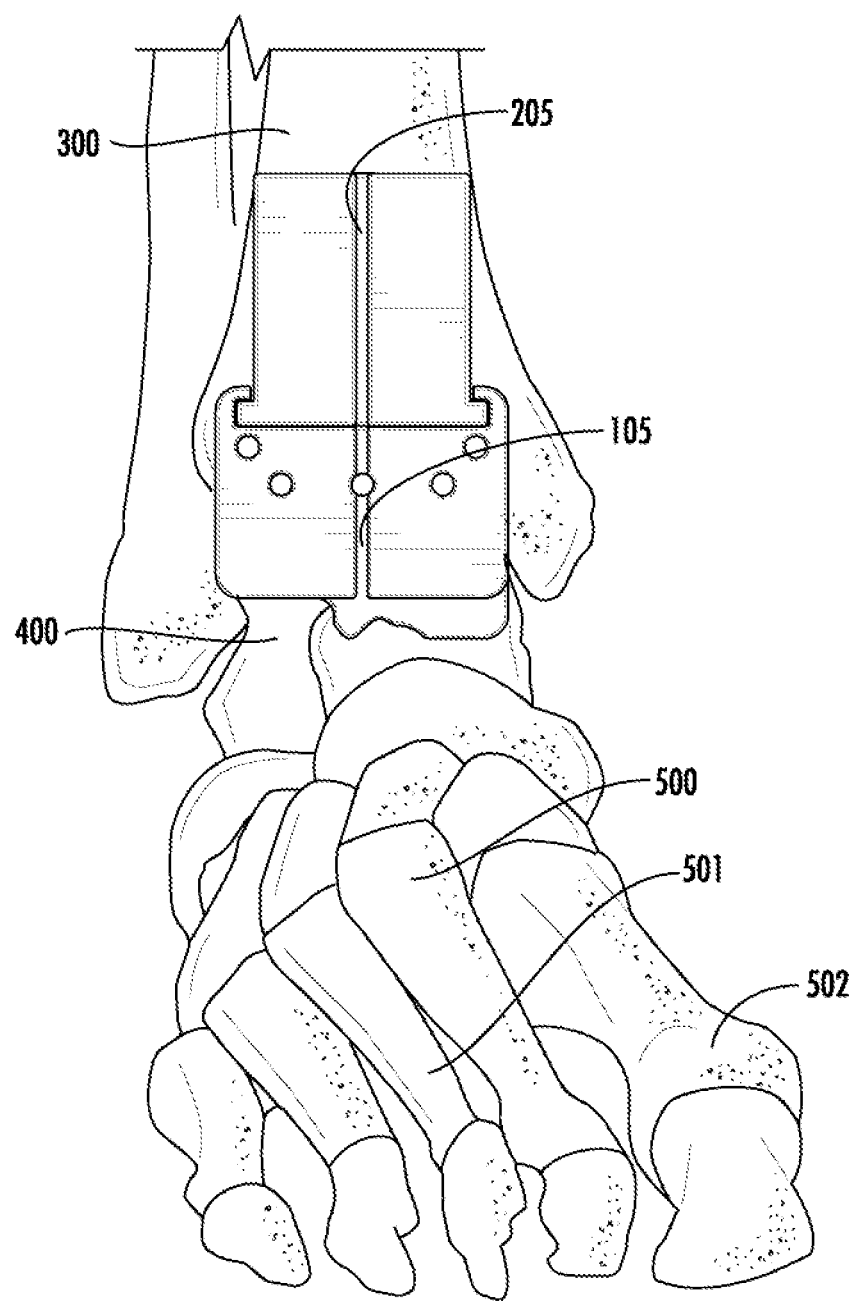
FIG. 4 is an anterior view of the first and second instruments in position relative to a patient's anatomy.

The first and second alignment features 105 and 205 can be used in conjunction with each other, as well as any other alignment reference or component. Visual markings or other indicia can be implemented with the first and second alignment features 105, 205. The first and second alignment features 105, 205 are shown in FIG. 4 relative to bones 500, 501, 502 in the patient's foot, as well as the tibia 300 and the talus 400. The alignment features 105, 205 generally aid in positioning the first and the second instruments 100, 200 relative to each other and/or the patient's anatomy.

In one aspect, the second surgical instrument 200 lacks any apertures or other openings configured to receive a K-wire or guide wire, and instead only includes the third bone contact interface 201, the second connection interface 202, and the second alignment feature 205.

In one aspect, both the first and the second instruments 100, 200 can be specifically formed or designed for an individual patient based on patient specific data. For example, digital image data may be obtained using imaging techniques, such as but not limited to X-rays, CT scans, MRIs, such that any one or more of the first, second, and third bone contact interfaces 101, 103, 201 replicate the patient's specific anatomy. In another aspect, at least one or both of the first and second bone contact interfaces 101, 103 on the first instrument 100 include patient specific profiles, and the third bone contact interface 201 on the second instrument 200 includes a generic bone contact interface. In one embodiment, surfaces 101 and 201 are generic and surface 103 is specifically modeled based on a patient's anatomy.

In one aspect, the bone contact interfaces 101, 103, and 201 are specifically formed or designed to match or complement the patient's anatomy. One of skill in the art would understand that other components of any of the instruments disclosed herein can be specifically selected or formed based on a patient's anatomy. Contact between the bone contact interfaces 101, 103, and 201 and the patient's bones 300, 400 is best shown in FIG. 5. As also shown in FIG. 5, outward surfaces (i.e. surfaces opposite from the bone contact regions) of the first and second instruments 100, 200 are aligned with each other once the instruments 100, 200 are in position.

Figure 6C:
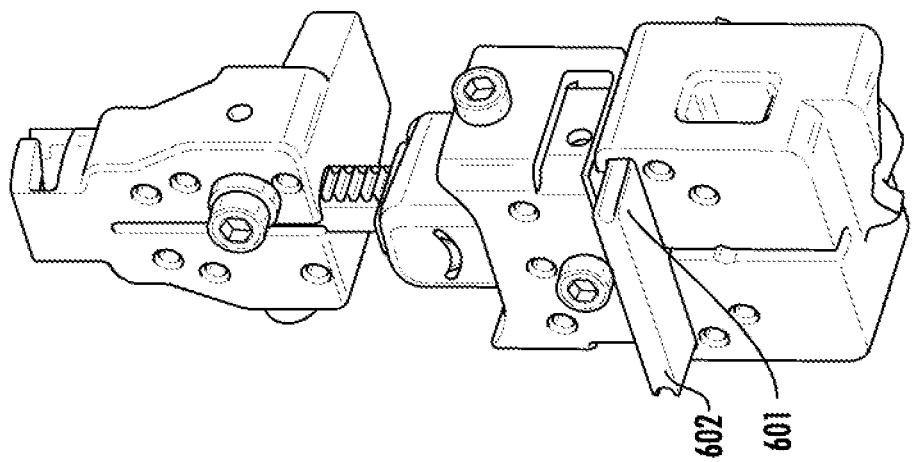
FIG. 6C is another perspective view of the first instrument and the third instrument from FIG. 6A.
Figure 6B:
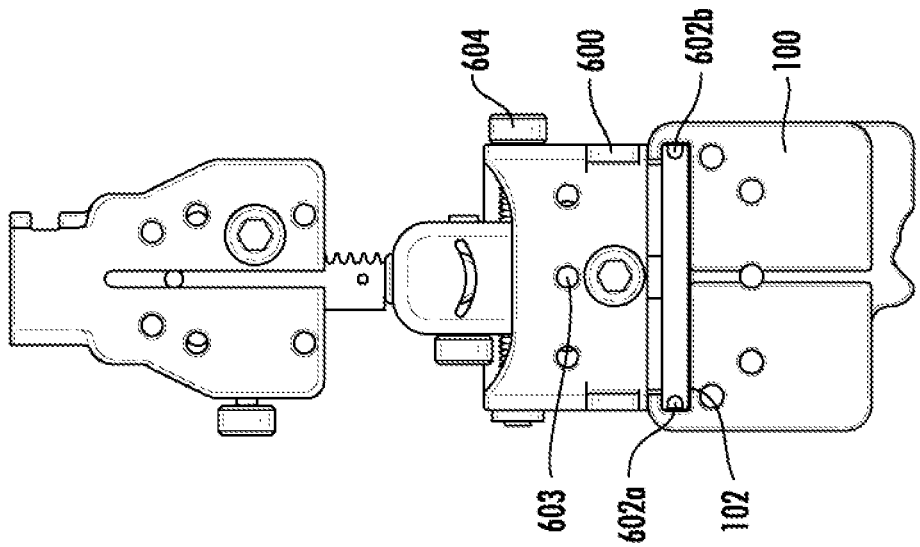
FIG. 6B is an anterior view of the first instrument and the third instrument from FIG. 6A.
Figure 6A:
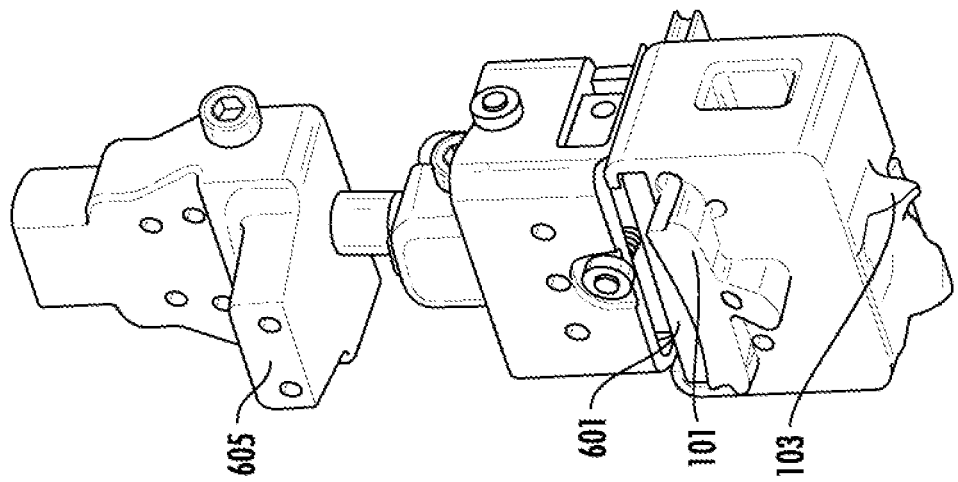
FIG. 6A is a perspective view of the first instrument and a third instrument mated with each other.

A third surgical instrument 600, shown in FIGS. 6A-6C, is also provided herein. The third instrument 600 generally includes a connection interface 601 (also referred to herein as a third connection interface 601) that is configured to mate, link, or otherwise join the third instrument 600 with another instrument, such as the first instrument 100. As shown in FIGS. 6A-6C, the third connection interface 601 can include a protrusion configured to be slid into the slot formed by the first connection interface 102 of the first instrument 100. The connection interface 601 is dimensioned to be received under the arms 102a, 102b of the first instrument 100. This arrangement ensures that the third instrument 600 is secured and fixed in position relative to the first instrument 100.

The third instrument 600 may also include another connection interface 602 (also referred to herein as a fourth connection interface 602) that is configured to allow the third surgical instrument 600 to mate with another instrument, such as a fifth surgical instrument 620. In one aspect, the third connection interface 601 and the fourth connection interface 602 can be formed on the same end or region of the third instrument 600. As shown in FIGS. 6A-6C, the fourth connection interface 602 can include a pair of apertures 602a, 602b configured to engage with a protrusion formed on another instrument.

Both the second and third instruments 200, 600 can be configured to connect to the same connection interface in one aspect, which can be the first connection interface 102 formed on the first surgical instrument 100. In another aspect, the second and third instruments 200, 600 can be configured to connect to different interfaces.

In one aspect, the third surgical instrument 600 includes at least one aperture 603, 603a, 603b, 603c, 603d, 603e, 603f, 603g configured to accept another surgical instrument or component (i.e. a fourth surgical instrument), such as a saw, drill k-wire, or a screw that is configured to engage a patient's anatomy or bone, such as bones 300 or 400.

The third instrument 600 may also comprise at least one adjustable mechanism 604, 604a, 604b, 604c, 604d configured to adjust positions of the apertures 603a, 603b, 603c, 603d, 603e, 603f, 603g relative to patient anatomy, such as bone 300, bone 400, or both.

The mechanisms 604, 604a, 604b, 604c, 604d can include a plurality of mechanisms that include a linkage, knob, adjuster, or other interface that can cause locking, or adjusting of a relative angle or position of an upper portion 600a of the third surgical instrument 600 to a lower portion 600b of the third surgical instrument 600.

In one aspect, the third surgical instrument 600 may generally correspond to the adjustment assembly 10, as disclosed in US Patent Pub. No. 2021/0077276, which is incorporated by reference as if fully set forth herein, and is commonly owned by Kinos Medical Inc. Certain functional and structural characteristics, as well as other features, of the third surgical instrument 600 may be similar to the adjustment assembly 10 as disclosed in US Patent Pub. No. 2021/0077276 unless otherwise specified herein. Alternatively, a completely different type of instrument or tool than disclosed in US Patent Pub. No. 2021/0077276 can be used in conjunction with the other instruments disclosed herein. In one aspect, certain features of the third surgical instrument 600 are different from the adjustment assembly 10 as disclosed in US Patent Pub. No. 2021/0077276.

In one aspect, the present disclosure allows for medial-lateral adjustment, which is linear adjustment in the coronal plane (i.e. same plane as *varus*-valgus). One skilled in the art would understand that various adjustments may be possible based on the instruments disclosed herein, and the adjustments are not limited to a single plane.

In one aspect, the present disclosure provides the ability to use a patient specific guide or instrument (such as the first instrument 100) to mate with a generic, i.e. not patient specific, instrument (such as the second instrument 200). The generic instrument may then be adjusted after the patient specific guide or instrument, i.e. the second instrument 200, is removed and the patient specific guide or instrument, i.e. instrument 100, remains attached to the patient to aid with alignment of another instrument, i.e. instrument 600, that is configured to attach to the patient specific guide or instrument.

In one aspect, the adjustment mechanisms 604, 604a, 604b, 604c, 604d are configured to adjust translation or rotation in a first plane, and adjust rotation or translation in a second plane that is oriented 90 degrees to the first plane. One adjustment mechanism can be configured to adjust rotation in a plane and another adjustment mechanism can be configured to adjust translation in that same plane.

Figures 7A, 7B:
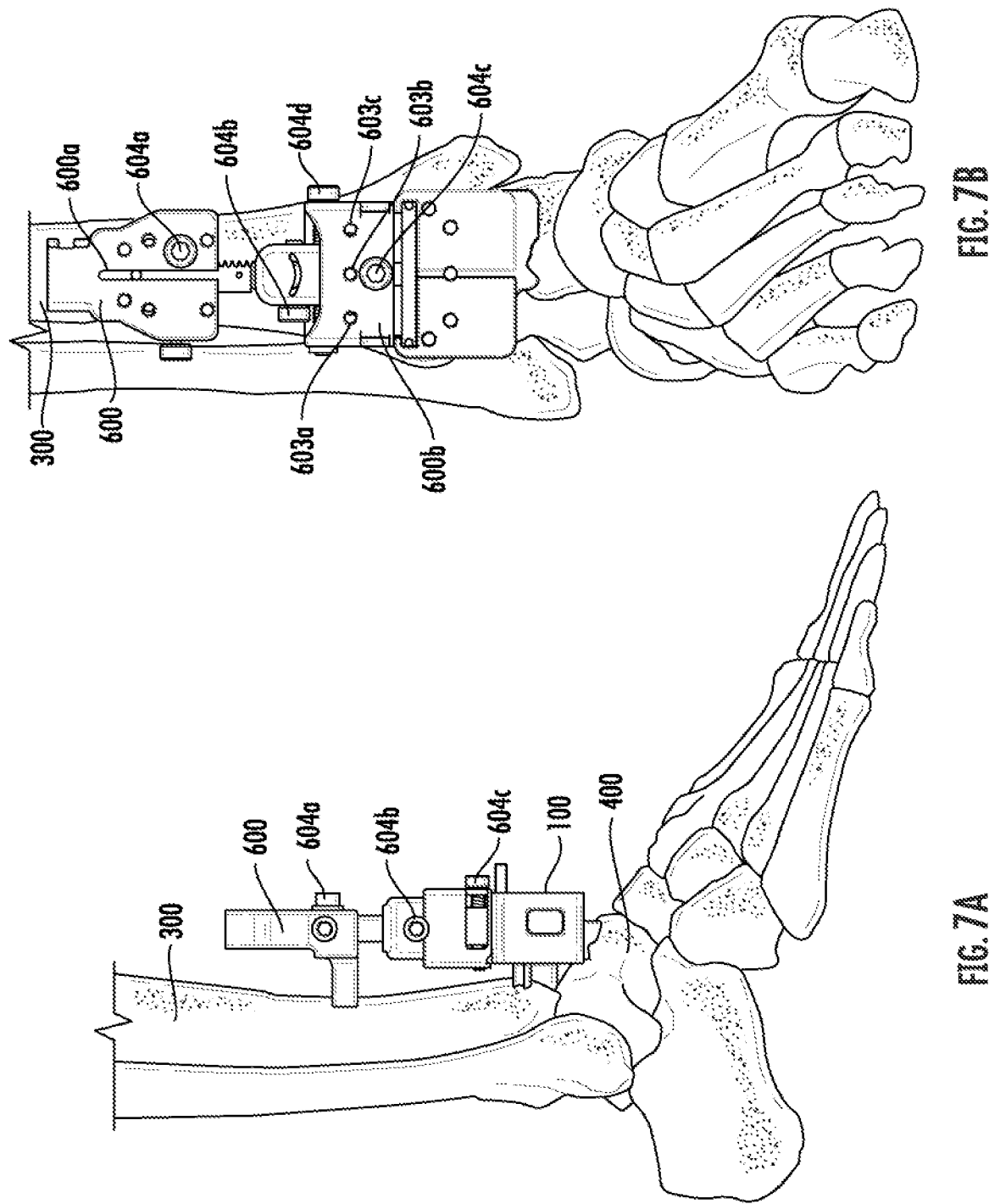
FIG. 7A is a lateral view of the first and third instruments deployed relative to a patient's anatomy.
FIG. 7B is an anterior view of the first and third instruments deployed relative to a patient's anatomy.

The third instrument 600 can also comprise a bone contact interface 605, i.e. a fourth bone contact interface). As show in FIG. 7A, the fourth bone contact interface 605 can be configured to contact bone 300, which may be the tibia. In one aspect, the bone contact interface 605 provides an anchoring configuration or fixed point of reference between at least one portion of the third instrument 600 and the bone that the third instrument 600 contacts. The bone contact interface 605 can also be configured to engage with another bone, such as bone 400. In one aspect, the bone contact interface 605 may be configured to contact any patient's bone or configured to mate with a specific patient's bone. The bone contact interface 605 can have a generic bone contacting profile, or may include a bone contacting profile that is specifically formed to match a specific patient's anatomy.

Figure 8C:
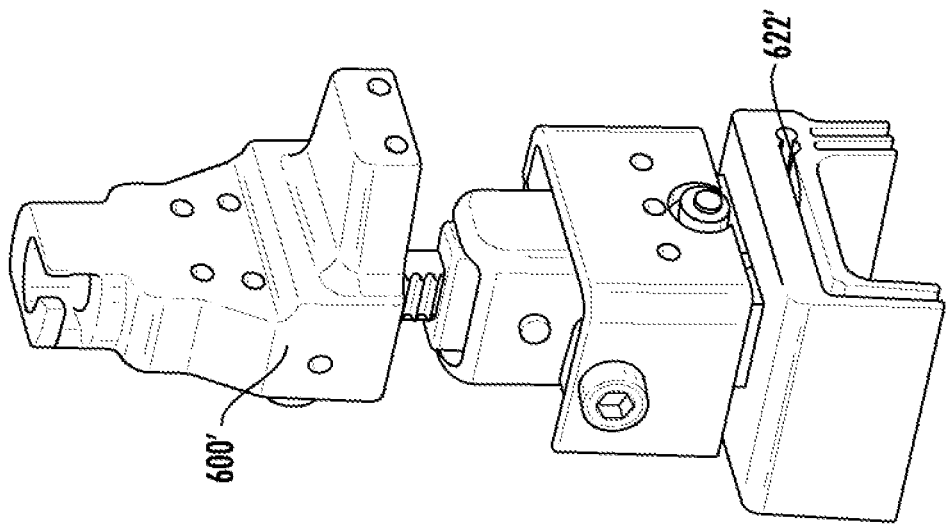
FIG. 8C is a perspective view of a third instrument according to one aspect.
Figure 8B:
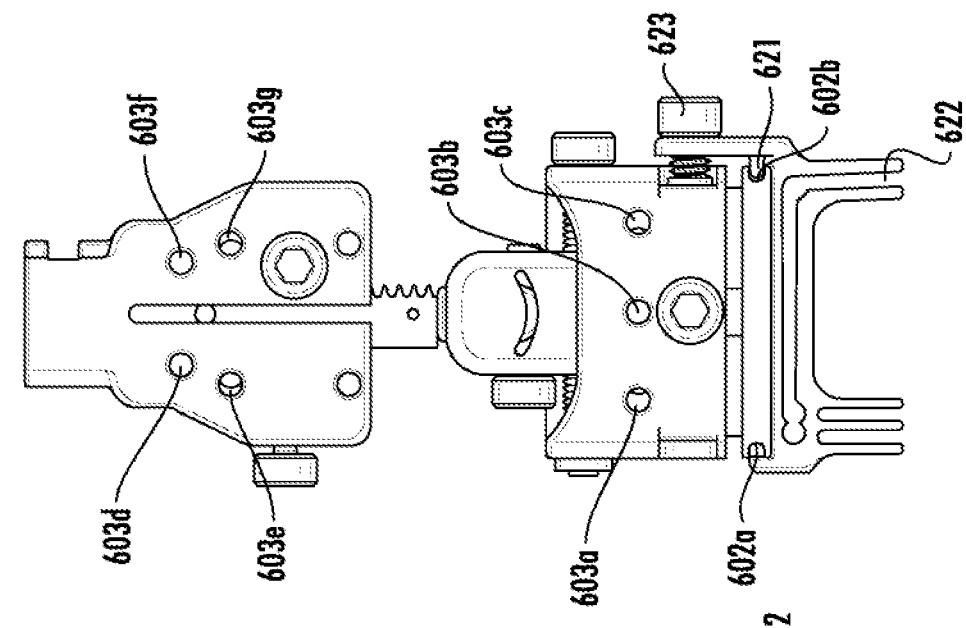
FIG. 8B is an anterior view of the third instrument connected to the fifth instrument.
Figure 8A:
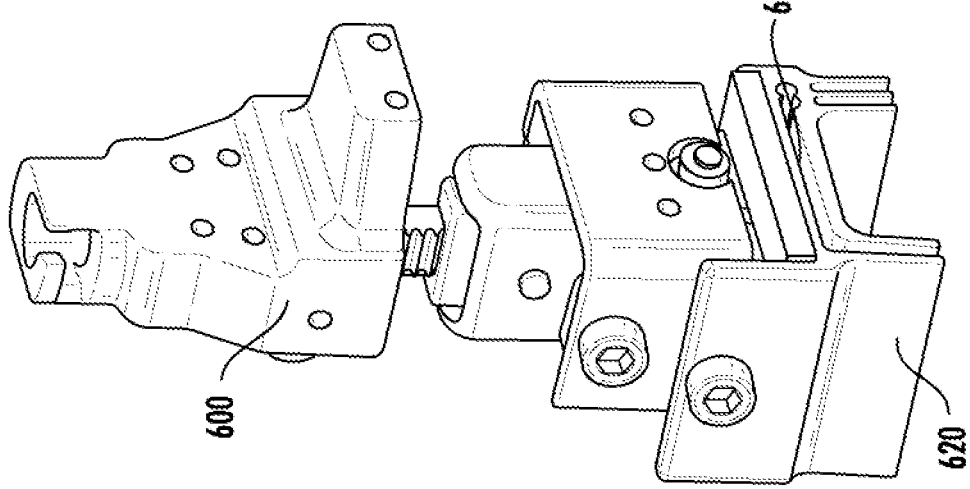
FIG. 8A is an isometric view of the third instrument connected to a fifth instrument.
Figure 9B:
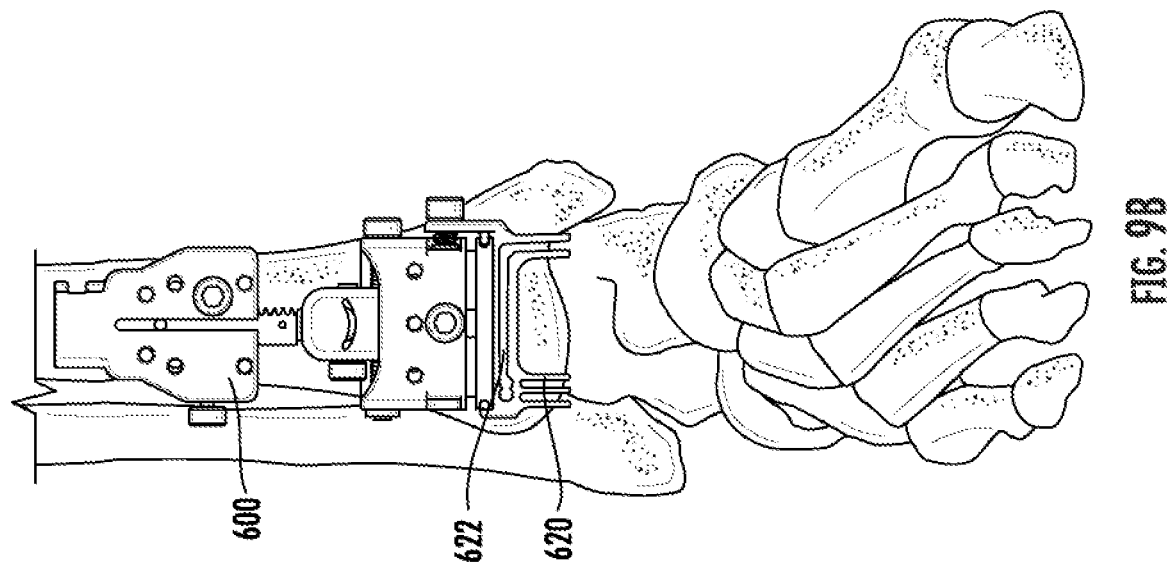
FIG. 9B is an anterior view of the third and fifth instruments connected to each other and deployed to a patient's anatomy.
Figure 9A:
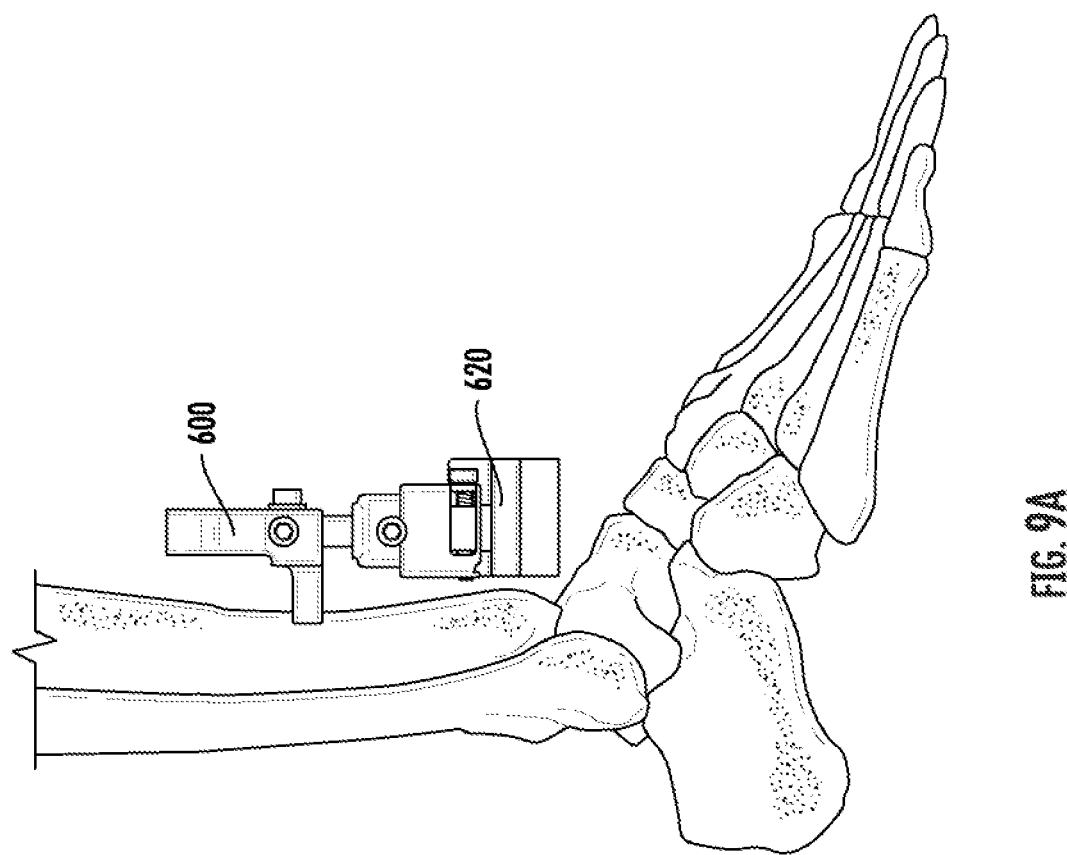
FIG. 9A is a lateral view of the third and fifth instruments connected to each other and deployed to a patient's anatomy.

The fifth instrument 620, as shown at least in FIGS. 8A and 8B, is generally configured to attach to a bottom region of the third instrument 600, in one aspect. The fifth instrument 620 comprises a connection interface 621, also referred to as a fifth connection interface, that is configured to allow the fifth instrument 620 to mate with the fourth connection interface 602 of the third instrument 600. Specifically, the connection interface 621 can be formed as a pair of protrusions configured to engage within the pair of apertures 602*a*, 602*b* of the third instrument 600.

The fifth instrument 620 may also comprise at least one guide opening 622, which may be formed as a slot, aperture, or other gap, that is configured to receive another surgical instrument 630 (i.e. a fourth surgical instrument), including but not limited to, a saw, drill, burr, wire, or screw. As shown in FIGS. 8A and 8B, the at least one guide opening 622 may include a plurality of slots or openings.

As shown in FIG. 8C, the third instrument 600' may include the at least one guide opening 622' instead of the opening being formed on a separate instrument, i.e. the fifth instrument 620. Another instrument or tool can be guided through the opening 622' formed integrally with the third instrument 600'

In one aspect, the fifth instrument 620 comprises a locking mechanism 623 used to securely and rigidly attach the fifth surgical instrument 620 to the third surgical instrument 600. Other adjustment assemblies or locking assemblies can be provided.

A surgeon can use adjustment mechanisms 604, 604*a*, 604*b*, 604*c*, 604*d* to specifically adjust a segment of the third surgical instrument 600 that contains the rigidly attached fifth surgical instrument 620. In moving at least one of the adjustment mechanisms 604, 604*a*, 604*b*, 604*c*, 604*d*, the surgeon can select the orientation that a fourth surgical instrument 630 will engage or intersect at least one of the bones, such as bones 300, 400, or any other bone. This effectively allows the surgeon to adjust the location of bone preparation completed on at least one bone (i.e. bones 300 or 400), such as bone removal, bone sawing, bone drilling, or other operations relative to the original placement of the first instrument 100, the second instrument 200, the bone 300, and/or the bone 400.

In one aspect, the fifth instrument 620 is configured to be modular with respect to the third instrument 600. In other words, the fifth instrument 620 can be provided in a variety of different sizes and having different configurations, each configured or fitting onto the third instrument 600. In another aspect, the fifth instrument 620 is formed integrally with the third instrument 600. In one aspect, the fifth instrument 620 lacks any bone contact surfaces or interfaces.

As shown in FIGS. 10A and 10B, in one aspect, the fourth instrument 630 may include a single instrument or tool, or more than one instrument or tool. In one aspect, the fourth instrument 630 includes at least one of a saw blade, drill, mill, k-wire, pin, or other surgical component.

In one aspect, the connection or mating interfaces (i.e. elements 102, 202, 601, 602, etc.) are all formed as generally rectangular protrusions, slots, or protrusions that mate with each other. In this manner, the instruments can easily be slid into mating contact with each other without requiring any tools or complex assembly steps. Additionally, the instruments are reliably secured to each other due to the elongated contact surfaces defined between the connection or mating interfaces, which generally are defined along at least an entire end surface of the respective instruments.

In one embodiment, a method of aligning at least one surgical instrument containing at least one aperture for guiding another surgical instrument is disclosed. The method includes placing at least one first instrument 100 and at least one second instrument 200 in contact with an at least one bone of a patient. The method includes connecting the at least one second instrument 200 to the at least one first instrument 100. In one aspect, the first and second instruments 100, 200 can be connected with each other prior to placement onto the bone. In other aspects, either one the first or second instruments 100, 200 can be independently attached or placed next to the bone prior to connection with the other instruments.

The method includes removing the at least one second instrument 200 from the at least one bone of a patient, and leaving the first instrument 100 in a desired alignment position relative to the patient. The method includes aligning at least one third instrument 600 with the at least one first instrument 100 and aligned with the at least one bone of the patient, and the at least one surgical instrument 600 is fixated to the at least one bone of the patient. The method includes guiding the at least one fourth instrument 630 through at least one aperture on the third instrument 600.

In another aspect, a method of aligning surgical instruments relative to a patient is provided. The method includes providing any one or more of the instruments disclosed herein. The method includes connecting the first instrument with the second instrument, and arranging the first instrument and the second instrument in contact with a patient's bony anatomy. The method includes removing the second instrument from the first instrument such that the first instrument remains engaged with the patient's bony anatomy. The method includes attaching the third instrument to the first instrument, and then removing the first instrument from the third instrument such that the third instrument remains engaged with the patient's bony anatomy.

In another aspect, a method of aligning at least one surgical instrument including at least one guide opening includes: (i) linking the at least one first surgical instrument and the at least one second surgical instrument with each other to form an assembly, (ii) arranging the assembly of the at least one first surgical instrument and the at least one second surgical instrument on a patient's bone, and (iii) removing the at least one second surgical instrument from the at least one bone of a patient, leaving the at least one first surgical instrument in a desired alignment position relative to the patient.

In one embodiment, a surgical guide assembly or configuration is provided that only includes the first and second instruments 100, 200.

The disclosed assembly and instruments allow for surgeons to place tools relative to a patient without relying on external guiding elements (i.e. K-wires or guide wires), and instead relying on the interfaces defined by the instruments with respect to the bone surfaces.

In one aspect, the disclosed subject matter provides for a set of modular instruments or tools that allows a surgeon to quickly and easily align specific tools or instruments relative to a patient's anatomy.

One of ordinary skill in the art would understand from this disclosure that any one or more of the embodiments can be used in connection with any one or more of the steps described herein.

Having thus described the present invention in detail, it is to be appreciated and will be apparent to those skilled in the art that many physical changes, only a few of which are exemplified in the detailed description of the invention, could be made without altering the inventive concepts and principles embodied therein.

It is also to be appreciated that numerous embodiments incorporating only part of the preferred embodiment are possible which do not alter, with respect to those parts, the inventive concepts and principles embodied therein.

The present embodiment and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

The invention claimed is:

1. A surgical guide comprising:
    a first surgical instrument comprising:
        a first bone contact interface configured to contact a tibia of a patient, and a second bone contact interface configured to contact a talus of the patient, and
        a first connection interface configured to mate with at least one connection interface formed on at least one other different surgical instrument, wherein the first connection interface is at least partially defined on an outer end surface of the first surgical instrument; and
    at least one additional surgical instrument configured to mate with the first connection interface, the at least one additional surgical instrument comprising
    at least one aperture for guiding another surgical instrument; and
    at least one adjustable mechanism configured to reposition the at least one aperture relative to the tibia of the patient,
    wherein the first surgical instrument is configured to contact the tibia and talus of the patient such that the first surgical instrument is oriented in a predetermined manner.

2. The surgical guide according to claim 1, wherein the at least one adjustable mechanism includes at least two adjustable mechanisms configured to reposition the at least one aperture.

3. The surgical guide according to claim 2, wherein the at least two adjustable mechanisms are configured to reposition the at least one aperture in two distinct planes that are oriented 90 degrees relative to each other.

4. The surgical guide according to claim 1, wherein the at least one additional surgical instrument includes a second connection interface configured to mate with the first connection interface, wherein the second connection interface is also configured to mate with a different connection interface formed on a surgical instrument different than the first surgical instrument.

5. The surgical guide according to claim 1, wherein the first surgical instrument and the at least one additional surgical instrument are positionable relative to the patient without any external guiding elements.

6. A method of aligning surgical instruments, the method comprising:
    providing a first surgical instrument including a first bone contact interface configured to contact a tibia of a patient and a second bone contact interface configured to contact a talus of the patient, and a first connection interface configured to mate with a connection interface formed on a different surgical instrument, wherein the first connection interface is at least partially defined on an outer end surface of the first surgical instrument;
    arranging the first surgical instrument on the tibia of the patient using the first bone contact interface;
    linking the first surgical instrument with at least one additional surgical instrument via engagement between the first connection interface and a second connection interface formed on the at least one additional surgical instrument to form an assembly;
    removing the first surgical instrument; and
    leaving the at least one additional surgical instrument in a desired alignment position relative to a patient, wherein the second connection interface formed on the at least one additional surgical instrument is configured to engage with a connection interface formed on another surgical instrument that is different than the first surgical instrument.

7. A method of aligning surgical instruments, the method comprising:
    providing a first surgical instrument including a first bone contact interface configured to contact a tibia of a patient and a second bone contact interface configured to contact a talus of the patient, and a first connection interface configured to mate with a connection interface formed on a different surgical instrument, wherein the first connection interface is at least partially defined on an outer end surface of the first surgical instrument;
    arranging the first surgical instrument on the tibia of the patient using the first bone contact interface; and
    linking the first surgical instrument with at least one additional surgical instrument via engagement between the first connection interface and a second connection interface formed on the at least one additional surgical instrument to form an assembly, wherein the at least one additional surgical instrument comprises at least one aperture for guiding another surgical instrument, and at least one adjustable mechanism configured to reposition the at least one aperture relative to the tibia of the patient.

8. The method according to claim 7, wherein the at least one adjustable mechanism includes at least two adjustable mechanisms configured to reposition the at least one aperture.

9. A method of aligning surgical instruments relative to a patient, the method comprising:
    providing a first surgical instrument including a first bone contact interface configured to contact a tibia of a patient, a second bone contact interface configured to contact a talus of the patient, and a first connection interface configured to mechanically link the first surgical instrument with at least one other surgical instrument, wherein the first connection interface is at least partially defined on an outer end surface of the first surgical instrument;

connecting the first surgical instrument with at least one additional surgical instrument, and arranging the first surgical instrument and the at least one additional surgical instrument in contact with the tibia of the patient; and removing the first surgical instrument from the at least one additional surgical instrument while the at least one additional surgical instrument remains in contact with the tibia of the patient.

10. The method according to claim 9, wherein the at least one additional surgical instrument comprises at least one aperture for guiding another surgical instrument, and at least one adjustable mechanism configured to reposition the at least one aperture relative to an anatomy of the patient.

11. The method according to claim 9, wherein the at least one additional surgical instrument comprises another connection interface configured to mate with both the first connection interface of the first surgical instrument and a different connection interface formed on a different surgical instrument.

\* \* \* \* \*